United States Patent [19]

Stoltefuss

[11] Patent Number: 5,476,940
[45] Date of Patent: Dec. 19, 1995

[54] 3-SUBSTITUTED QUINOLINE-5-CARBOXYLIC ACIDS

[75] Inventor: Jürgen Stoltefuss, Haan, Germany

[73] Assignee: Bayer Aktiengesellschaft, Leverkusen, Germany

[21] Appl. No.: 128,955

[22] Filed: Sep. 29, 1993

[30] Foreign Application Priority Data

Oct. 6, 1992 [DE] Germany ............... 42 33 601.5

[51] Int. Cl.$^6$ ............... C07D 215/14; C07D 215/20; C07D 215/36; C07D 401/08
[52] U.S. Cl. ............... 546/153; 546/167; 546/170
[58] Field of Search ............... 546/153, 170, 546/167

[56] References Cited

U.S. PATENT DOCUMENTS

| | | | |
|---|---|---|---|
| 4,769,375 | 9/1988 | Meyer | 514/311 |
| 5,068,337 | 11/1991 | Archibald | 514/256 |
| 5,100,900 | 3/1992 | Stoltefuss | 514/314 |
| 5,204,472 | 4/1993 | Stoltefuss | 546/168 |
| 5,210,231 | 5/1993 | Stoltefuss | 549/304 |
| 5,262,429 | 11/1993 | Stoltefuss | 514/314 |
| 5,270,469 | 12/1993 | Stoltefuss | 514/170 |

FOREIGN PATENT DOCUMENTS

| | | |
|---|---|---|
| 452712 | 3/1991 | European Pat. Off. . |
| 476474 | 9/1991 | European Pat. Off. . |

OTHER PUBLICATIONS

Stoltefuss, J., CA 117(9)90123d, abstract of EP 476474, Mar. 1992.
Makriyannis, A., "3–Phenyl–5–Quinolinemethanol Antimalarials", J Med Chem, vol. 16, No. 2, pp. 118–122, 1973.
General Chemistry, Week 8448, p. 2, J5 9184–161–A–Derwent Abstract, Oct. 1984.
Derwent Abstract, Week 8848, AN 84–297394 & JP–A–59 184 161, Oct. 19, 1984.

*Primary Examiner*—C. Warren Ivy
*Assistant Examiner*—D. Margaret M. Mach
*Attorney, Agent, or Firm*—Sprung Horn Kramer & Woods

[57] ABSTRACT

The present invention relates to novel 3-substituted quinoline-5-carboxylic acids, a process for their preparation and their use in the preparation of 4-quinolyl-dihydropyridines.

7 Claims, No Drawings

3-SUBSTITUTED QUINOLINE-5-CARBOXYLIC ACIDS

The present invention relates to novel 3-substituted quinoline-5-carboxylic acids, a process for their preparation and their use in the preparation of 4-quinolyl-dihydropyridines.

The compound 3-phenyl-5-quinolinecarboxylic acid is known from the publication DE 40 298 07, while the corresponding 3-methyl-substituted compound is listed in JP 59 184 161.

In addition, some compounds according to the invention are included within the scope of the meaning of an intermediate of EP 452 712, without a concrete representative compound being mentioned in that patent.

The present invention relates to novel 3-substituted quinoline-5-carboxylic acids of the general formula (I)

in which
$R^1$ represents straight-chain or branched alkyl having 2 to 8 carbon atoms, or represents a radical of the formula —A—$R^2$,
in which
A denotes a single bond, an oxygen or sulphur atom or an alkylidene chain having up to 3 C atoms,
and
$R^2$ denotes pyridyl or phenyl, which is optionally substituted identically or differently up to 3 times by nitro, halogen, trifluoromethyl, or by straight-chain or branched alkyl, alkoxy or alkoxycarbonyl having in each case up to 8 carbon atoms, hydroxyl or carboxyl,
where, in the case where A represents a single bond, $R^2$ does not represent unsubstituted phenyl,
and salts thereof.

Compounds of the general formula (I) are preferred in which
$R^1$ represents straight-chain or branched alkyl having from 2 to 6 carbon atoms, or represents a radical of the formula —A—$R^2$,
in which
A denotes a single bond, an oxygen or sulphur atom or an alkylidene chain having up to 2 C atoms
and
$R^2$ denotes pyridyl or phenyl, which is optionally substituted identically or differently up to 2 times by nitro, fluorine, chlorine, bromine, trifluoromethyl, or by straight-chain or branched alkyl, alkoxy or alkoxycarbonyl having in each case up to 6 carbon atoms,
where, in the case where A represents a single bond, $R^2$ does not represent unsubstituted phenyl,
and salts thereof.

Compounds of the general formula (I) are particularly preferred
in which
$R^1$ represents straight-chain or branched alkyl having 2 to 4 carbon atoms, or represents a radical of the formula —A—$R^2$,
in which
A denotes a single bond, an oxygen or sulphur atom or the —$CH_2$— group
and
$R^2$ denotes pyridyl or phenyl, which is optionally substituted identically or differently up to 2 times by nitro, fluorine, chlorine, trifluoromethyl, or by straight-chain or branched alkyl, alkoxy or alkoxycarbonyl having in each case up to 4 carbon atoms,
where, in the case where A represents a single bond, $R^2$ does not represent unsubstituted phenyl,
and salts thereof.

Compounds of the general formula (I) are very particularly largely preferred
in which
$R^1$ represents n-butyl, i-propyl or tert-butyl, or represents a radical of the formula —A—$R^2$,
in which
A denotes a single bond, an oxygen or sulphur atom or the —$CH_2$— group
and
$R^2$ denotes pyridyl or phenyl, which is optionally substituted identically or differently up to 2 times by fluorine, chlorine, nitro, methyl, methoxy or methoxycarbonyl,
where, in the case where A represents a single bond, $R^2$ does not represent unsubstituted phenyl,
and salts thereof.

In addition, a process for preparing the compounds according to the invention of the general formula (I) has been found, characterised in that
4-amino-3-hydroxyphthalide of the formula (II)

is reacted with aldehydes of the general formula (III)

$$R^1—CH_2—CHO \quad \text{(III)}$$

in which
$R^1$ has the abovementioned meaning, in inert solvents.

By way of example, the process according to the invention can be illustrated by the following formula diagram:

All inert organic solvents which are not altered under the reaction conditions are suitable solvents for this process. These preferably include alcohols, such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoric triamide or dimethylformamide, or acetic acid or halogenated hydrocarbons such as methylene chloride or carbon tetrachloride or hydrocarbons such as benzene or toluene, as well as esters such as, for example, ethyl acetate. It is likewise possible to use mixtures of the said solvents. Methanol, isopropanol, ethanol and n-propanol, acetonitrile, tetrahydrofuran or diethylene glycol dimethyl ether are preferred.

The reaction temperatures can be varied over a wide range. In general, the work is carried out between +20° C. and +150° C. preferably between 60° C. and 120° C., in particular at the boiling temperature of the solvent concerned.

The reaction can be carried out under atmospheric pressure, but also under elevated pressure (e.g. 1 to 50 bar). In general, atmospheric pressure is employed.

The compound of the formula (II) is known [cf. DE 40 298 07].

The aldehydes of the general formula (III) are known in some cases, or can be prepared by known methods.

The above preparation process is given solely for clarification. The preparation of the compound of the formula (I) according to the invention is not limited to this process, but on the contrary any modification of this process, for example the use of nitro-amino reduction methods known from the literature, can be used in the same way for preparing the compound according to the invention.

The compounds according to the invention are of great importance for 1,4-dihydropyridine chemistry, since they are valuable intermediates for the synthesis of 4-quinolyl-dihydropyridines [cf. in this connection e.g. EP 452 712].

STARTING COMPOUNDS

EXAMPLE Z1

4-Amino-3-hydroxyphthalide

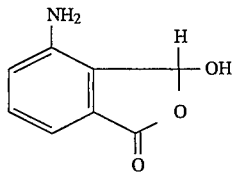

10 g of 3-hydroxy-4-nitro-phthalide are dissolved in 100 ml of tetrahydrofuran and, after the addition of 1 g of palladium on barium sulphate (5%), hydrogenated under atmospheric pressure and at 20°–50° C. The solution is filtered to remove the catalyst and concentrated. The evaporation residue is stirred with ether and filtered with suction. 5.8 g (68.5% of theory) of a colourless substance are obtained with a melting point of 280°–285° C. (decomp.).

PREPARATION EXAMPLES

EXAMPLE 1

3-Phenoxy-quinoline-5-carboxylic acid

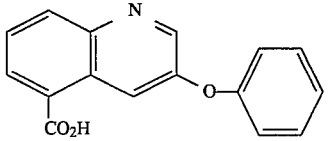

50 g (0.256 mol) of 3-hydroxy-4-nitro-phthalide are hydrogenated in 250 ml of ethanol using 5 g of palladium/barium sulphate (5%) at 40° C. to 50° C. and under 3.5 bar. The solution is filtered with suction, 45 g (0.33 mol) of phenoxyacetaldehyde are added to the filtrate, and the mixture is then boiled for 20 hours. The precipitated product is, after cooling, filtered off with suction and washed with ethanol. 25.5 g (36.85% of theory) are obtained with a melting point of >250° C.

The examples listed in Table 1 are prepared in analogy to the instructions of Example 1:

TABLE 1

| Example no. | R¹ | m.p.(°C.) |
|---|---|---|
| 2 | 2-Cl-phenyl | >280 |
| 3 | 3-Cl-phenyl | >280 |
| 4 | 4-Cl-phenyl | >280 |
| 5 | 2-F-phenyl | >280 |
| 6 | 3-F-phenyl | >280 |
| 7 | 4-F-phenyl | 336 (decomp.) |

TABLE 1-continued

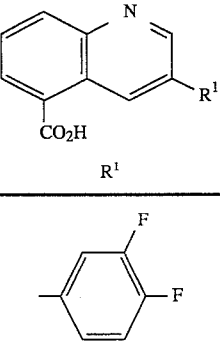

| Example no. | R¹ | m.p.(°C.) |
|---|---|---|
| 8 | 3,4-difluorophenyl | >280 |
| 9 | 2-(trifluoromethyl)phenyl | >280 |
| 10 | 2-methylphenyl | >280 |
| 11 | 3-methylphenyl | >250 |
| 12 | 4-methylphenyl | >280 |
| 13 | 3-nitrophenyl | >280 |
| 14 | 4-nitrophenyl | >250 |
| 15 | 2-methoxyphenyl | >250 |
| 16 | 3-methoxyphenyl | 186–188 (decomp.) |
| 17 | 4-methoxyphenyl | >250 |
| 18 | 3,4-dimethoxyphenyl | 287–290 (decomp.) |
| 19 | —H₂C—phenyl | 278–280 |
| 20 | —O—(4-chlorophenyl) | 290–291 |
| 21 | 4-(CO₂CH₃)phenyl | >280 |
| 22 | 4-pyridyl | >250 |
| 23 | —S—phenyl | 287–288 |
| 24 | —H₂C-(2-pyridyl) | 190 |
| 25 | —H₂C-(4-methoxyphenyl) | 285–286 |
| 26 | —C(CH₃)₃ | 150 |
| 27 | -n-C₄H₉ | 230 (decomp.) |
| 28 | —CH(CH₃)₂ | 284–86 |

I claim:
1. 3-substituted quinoline-5-carboxylic acids of the general formula (I)

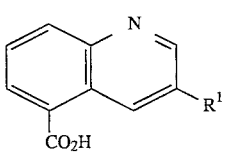

(I)

in which $R^1$ represents straight-chain or branched alkyl having 2 to 8 carbon atoms, or represents a radical of the formula —A—$R^2$, in which A denotes an oxygen or sulphur atom or an alkylidene chain having up to 3 C atoms, and $R^2$ denotes pyridyl or phenyl, which is optionally substituted identically or differently up to 3 times by nitro, halogen, trifluoromethyl, or by straight-chain or branched alkyl, alkoxy or alkoxycarbonyl having in each case up to 8 carbon atoms, hydroxyl or carboxyl, or salts thereof.

2. Compounds of the general formula (I) according to claim 1, in which $R^1$ represents straight-chain or branched alkyl having from 2 to 6 carbon atoms, or represents a radical of the formula —A—$R^2$, in which A denotes an oxygen or sulphur atom or an alkylidene chain having up to 2 C atoms and $R^2$ denotes pyridyl or phenyl, which is optionally substituted identically or differently up to 2 times by nitro, fluorine, chlorine, bromine, trifluoromethyl, or by straight-chain or branched alkyl, alkoxy or alkoxycarbonyl having in each case up to 6 carbon atoms, or salts thereof.

3. Compounds of the general formula (I) according to claim 1, in which $R^1$ represents straight-chain or branched alkyl having 2 to 4 carbon atoms, or represents a radical of the formula —A—$R^2$, in which A denotes an oxygen or sulphur atom or the —$CH_2$— group and $R^2$ denotes pyridyl or phenyl, which is optionally substituted identically or differently up to 2 times by nitro, fluorine, chlorine, trifluoromethyl, or by straight-chain or branched alkyl, alkoxy or alkoxycarbonyl having in each case up to 4 carbon atoms, or salts thereof.

4. Compounds of the general formula (I) according to claim 1, in which $R^1$ represents n-butyl, i-propyl or tert-butyl, or represents a radical of the formula —A—$R^2$, in which A denotes an oxygen or sulphur atom or the —$CH_2$— group and $R^2$ denotes pyridyl or phenyl, which is optionally substituted identically or differently up to 2 times by fluorine, chlorine, nitro, methyl, methoxy or methoxycarbonyl, and salts thereof.

5. A compound according to claim 1, wherein $R^1$ is —A—$R^2$ and A is an oxygen atom or a sulphur atom.

6. A compound according to claim 1, wherein $R^1$ is a straight-chain or branched alkyl having 2 to 8 carbon atoms.

7. A compound according to claim 1, wherein $R^1$ is —A—$R^2$ and A represents an alkylidene chain having up to 3 C atoms.

* * * * *

UNITED STATES PATENT AND TRADEMARK OFFICE
CERTIFICATE OF CORRECTION

PATENT NO.  : 5,476,940
DATED       : December 19, 1995
INVENTOR(S) : Jurgen Stoltefuss It is certified that error appears in the above-indentified patent and that said Letters Patent is hereby corrected as shown below:

Col. 8, line 25   Delete " and " and substitute -- or --

Signed and Sealed this

Eleventh Day of June, 1996

*Attest:*

BRUCE LEHMAN

*Attesting Officer*  *Commissioner of Patents and Trademarks*